United States Patent [19]

Ogden et al.

[11] Patent Number: 5,415,528
[45] Date of Patent: May 16, 1995

[54] SOLUTION PUMPING FOR MAXIMIZING OUTPUT WHILE MINIMIZING UNEVEN PUMPING PRESSURES

[75] Inventors: John E. Ogden, Libertyville; Edward Tripp, Antioch; William L. Rudzena, McHenry, all of Ill.

[73] Assignee: Abbott Laboratories, Abbott Park, Ill.

[21] Appl. No.: 303,279

[22] Filed: Sep. 8, 1994

Related U.S. Application Data

[63] Continuation of Ser. No. 993,167, Dec. 18, 1992.

[51] Int. Cl.[6] .................. A61M 5/142; F04B 49/08
[52] U.S. Cl. ....................... 417/28; 417/44.1; 417/44.8; 604/67; 128/DIG. 12; 318/645
[58] Field of Search .......... 417/19, 20, 28, 44.1, 417/44.3, 44.8; 604/151, 152, 153, 65, 67; 128/DIG. 12; 318/644, 645, 481; 222/63

[56] References Cited

U.S. PATENT DOCUMENTS

| | | | |
|---|---|---|---|
| 3,985,467 | 10/1976 | Lefferson | 417/20 |
| 4,137,913 | 2/1979 | Georgi | 604/152 |
| 4,468,219 | 8/1984 | George et al. | 604/67 |
| 4,474,309 | 10/1984 | Solomon | 604/152 |
| 4,840,542 | 6/1989 | Abbott | 417/28 |
| 4,919,649 | 4/1990 | Timothy et al. | 604/151 |
| 5,062,774 | 11/1991 | Kramer et al. | 128/DIG. 12 |
| 5,108,367 | 4/1992 | Epstein et al. | 604/153 |

FOREIGN PATENT DOCUMENTS 284979 12/1987 Japan .................... 417/19

*Primary Examiner*—Richard A. Bertsch
*Assistant Examiner*—Roland G. McAndrews, Jr.
*Attorney, Agent, or Firm*—A. Nicholas Trausch

[57] ABSTRACT

A solution pumping system is disclosed which is embodied as a disposable pump cassette including a self-contained positive displacement pump, and an associated pump driver including a reciprocable pump piston for driving the pump of the cassette. This system is particularly suited for use in compounding in preparation of parenteral solutions for administration to patients. In order to promote high liquid output with minimum peak pumping pressures, the controls of the system operate to provide a "square" pumping pressure waveform, thus optimizing performance of the system. This is achieved by selectively varying the velocity of the pump piston during its operation.

11 Claims, 3 Drawing Sheets

SOLUTION PUMPING FOR MAXIMIZING OUTPUT WHILE MINIMIZING UNEVEN PUMPING PRESSURES

This application is a continuation of Ser. No. 07/993,167, filed Dec. 18, 1992.

TECHNICAL FIELD

The present invention generally relates to a solution pumping system which can be advantageously employed for preparation of patient parenteral solutions, with controls of the system operating to provide a "square" waveform of pumping pressure, thereby acting to minimize peak pumping pressures, while maximizing liquid output.

BACKGROUND OF THE INVENTION

Healthcare facilities require preparation and administration of very large numbers of parenteral solutions for patients. Such solutions are administered for both nutritional and therapeutic purposes, and thus efficient liquid-handling systems are required for cost-effective preparation of such solutions, and their administration to patients.

To this end, positive displacement fluid pumping devices have been developed for both preparation and administration of parenteral solutions. Such devices permit precise control during pumping of solutions, thus facilitating solution administration and preparation.

U.S. Pat. Nos. 4,639,245, to Pastrone et al., 4,818,186, to Pastrone et al., and 4,842,584, to Pastrone, all of which are hereby incorporated by reference, disclose a positive displacement fluid infusion pumping device and components thereof, which have met with widespread acceptance by the healthcare industry. This pumping system includes a combination of a pump driver and an associated removable and disposable pump cassette. The pump cassette includes a self-contained positive displacement pump device, which is operated by a reciprocable pump plunger or piston of the associated pump driver. The pump driver includes selectively operable valve actuators, which cooperate with valve mechanisms provided in the pump cassette for accurate and highly automated administration and infusion of parenteral solutions.

Commonly-assigned U.S. patent application Ser. No. 07/444,459, filed Dec. 1, 1989, now U.S. Pat. No. 5,064,774 issued Nov. 11, 1991, discloses a solution pumping system generally of the above type, including a disposable pump cassette, and an associated pump driver. The system of this application is particularly configured for automatic compounding and preparation of parenteral solutions, for subsequent infusion to a patient. This application is hereby incorporated by reference.

Solution pumping systems of the above type employ pre-assembled, disposable pump cassettes. Typically, such pump cassettes include a cassette body having juxtaposed front and rear body members, between which is positioned a membrane-like elastomeric diaphragm. The diaphragm cooperates with the front body member to provide valve mechanisms at various inlets and outlets defined by the front body member, with openings in the rear body member exposing the diaphragm for operation of the valve mechanisms by valve actuators of the associated pump driver.

Additionally, the front body member of the cassette defines a pump chamber, which, together with the internal diaphragm, provides the self-contained positive displacement pump of the cassette. The rear body member defines an opening through which a reciprocable pump piston of the associated driver is movable for operating the cassette, whereby liquid can be pumped through the cassette.

To promote efficiency, it is desirable that when pumping systems of the present type are used for compounding and preparation of parenteral solutions, that the systems be operated with relatively high output of liquid flow, without sacrifice of precision. However, experience has shown that operating of such cassettes at relatively high pressures (which pressures can vary in direct relationship to the viscosity of a liquid), to promote efficient use can be problematical. High pumping pressures require a high degree of sealing integrity within the cassette structure, which can complicate efficient manufacture of the cassettes for disposable use.

Additionally, the pump cassette, as well as the associated tubing and other components through which liquid is pumped, is a so-called compliant system. In other words, by virtue of the flexible and resilient nature of the pump cassette diaphragm, the associated tubing, seals, and the like, the entire system exhibits compliance, or flexing, in response to the creation of liquid pressure within the cassette.

As will be appreciated, such compliance complicates precise and accurate pumping of liquids, creating cyclically undulating pressures within the cassette, attendant to operation, which undulations and instabilities must be stabilized for accurate operation. Of course, this requires providing sufficient periods of time for pressure stabilization during each pumping cycle so that pressure instabilities subside, thereby undesirably increasing the length of each cycle. As will be recognized, the degree of compliance exhibited by the system is directly related to the magnitude of pumping pressures created within the cassette, with reduced pressures desirably resulting in reduced system compliance.

The present solution pumping system promotes efficient and precise operation by minimizing peak pumping pressures, while optimizing liquid output.

SUMMARY OF THE INVENTION

The present solution pumping system, illustrated in the form of a disposable pump cassette and associated pump driver, promotes efficient and accurate solution pumping by creating a "square" pumping pressure waveform during each cycle of operation. While the pressure waveform is not truly "square" (a practical impossibility), liquid output is maximized by operating the system to very quickly reach peak operating pressure, maintaining that pressure for a sufficient period to effect the desired liquid displacement, and thereafter completing the pumping cycle as quickly as possible, within the physical limitations of the system. Thus, any "spikes" or the like in system pressure are avoided, desirably maintaining sealing integrity and minimizing system compliance, while at the same time maximizing liquid output of the system.

The illustrated embodiment of the present invention is in the form of a solution pumping system particularly configured for compounding and preparation of parenteral solutions. As such, the system includes a pump driver, including a reciprocable pump piston and a plurality of actuators, and a disposable pump cassette positionable in operative association with the pump driver. The pump cassette includes at least one, and preferably a plurality of liquid inlets, at least one liquid outlet, and a liquid flow path for joining a selected one of the inlets and the outlet in fluid communication.

The pump cassette further includes a self-contained positive displacement pump which is operatively driven by the pump piston of the associated pump driver. By coordinating operation of appropriate ones of the valve actuators of the pump driver with advancing and return strokes of the pump piston, liquid is pumped through the cassette.

While the present invention is particularly suited for use in preparing parenteral solutions, it will be recognized that a pumping system configured in accordance with the principles disclosed herein can be used for a wide variety of applications including infusion of parenteral solutions, wherein it is desired to limit peak pumping pressures while maximizing liquid output.

In accordance with the illustrated embodiment, the pump cassette includes a cassette body within which is positioned a membrane-like elastomeric diaphragm. The diaphragm cooperates with the cassette body to define the flow path therethrough, and further cooperates with the cassette body to provide valve elements for the various liquid inlets and outlets of the construction.

In order to effect liquid pumping, the cassette body includes a bowl-like pump chamber, with the diaphragm of the cassette including a resilient pump portion positioned adjacent to the pump chamber. During use of the system, the pump cassette is positioned in operative association with the pump driver such that the resilient pump portion of the diaphragm is positioned for engagement with the pump piston. In this manner, the diaphragm is displaced into the pump chamber during an advancing stroke of the pump piston, with the chamber refilled with liquid during a return stroke of the pump piston as the resilient diaphragm creates a negative pressure within the chamber.

In accordance with the present invention, the present solution pumping system includes programmable controls which control operation of the positive displacement pump by controlling the velocity of the pump piston of the pump driver. The controls act to minimize peak pressures created by the pump, during the advancing stroke of the pump piston, while maximizing liquid output of the pump. This is achieved by creating a relatively straight-sided, "square" pressure waveform during the advancing stroke of the piston. Such a waveform can be achieved by rapidly accelerating the piston to its maximum desired velocity, then decreasing the velocity for a selected interval to achieve complete displacement of liquid from the pump chamber, and thereafter controlling the return stroke of the piston so that the resilient pump diaphragm creates a negative pressure for refilling the chamber with liquid. Thus, the present system functions to selectively vary the velocity of the pump piston during each advancing stroke, and preferably also during each return stroke of the piston.

In the preferred form, the system includes a pressure sensor for sensing liquid pressure created by the positive displacement pump within the pump cassette. Desirably, the provision of a pressure sensor, operatively connected with the controls of the system, permits the system to automatically adapt to solutions having varying viscosities while avoiding the creation of undesirably high pressures within the pump cassette. The pressure sensor is preferably arranged to cooperate with the controls such that in the event that an undesirably high pressure is sensed, the controls alter the velocity characteristics of the pump piston (i.e., the "piston profile"), thus adjusting the "pressure profile" of the system to avoid creating high pressures, while still maximizing output.

Other features and advantages of the present invention will become readily apparent from the following detailed description, the accompanying drawings, and the appended claims.

DETAILED DESCRIPTION

Figure 1:
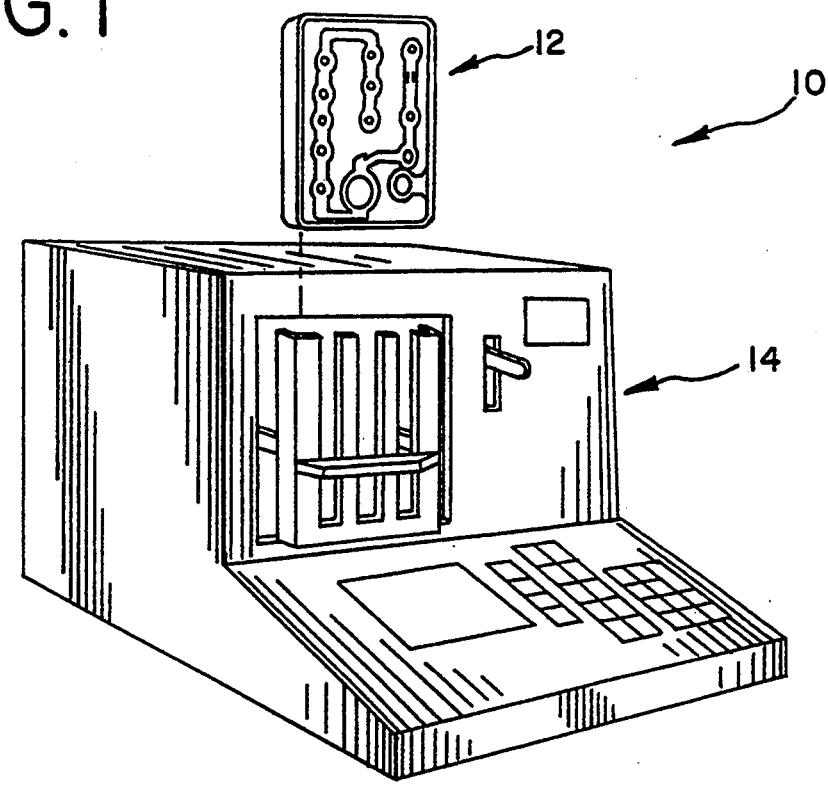
FIG. 1 is a perspective view of a solution pumping system, including a pump driver and a disposable pump cassette, embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawings, therein is illustrated a solution pumping system 10 embodying the principles of the present invention. The illustrated embodiment is shown in the form of a so-called solution compounder, that is, a system particularly suited for compounding and preparation of parenteral solutions for subsequent administration to patients. However, it will be appreciated that a system embodying the principles disclosed herein can be readily configured for infusion of such solutions, or for other applications.

The solution pumping system includes a disposable pump cassette 12 which is removably positionable in operative association with a pump driver 14. For use in compounding parenteral solutions, the system is joined, via appropriate tubing sets, with containers of solutions to be compounded, and with a container into which appropriate quantities of the various solutions are mixed. The resultant admixture is thus ready for patient administration. Because this type of system is capable of efficiently and accurately preparing very large numbers of such admixtures, the system would ordinarily be used in the pharmacy of a healthcare facility, preferably within a laminar-flow hood.

Figure 2:
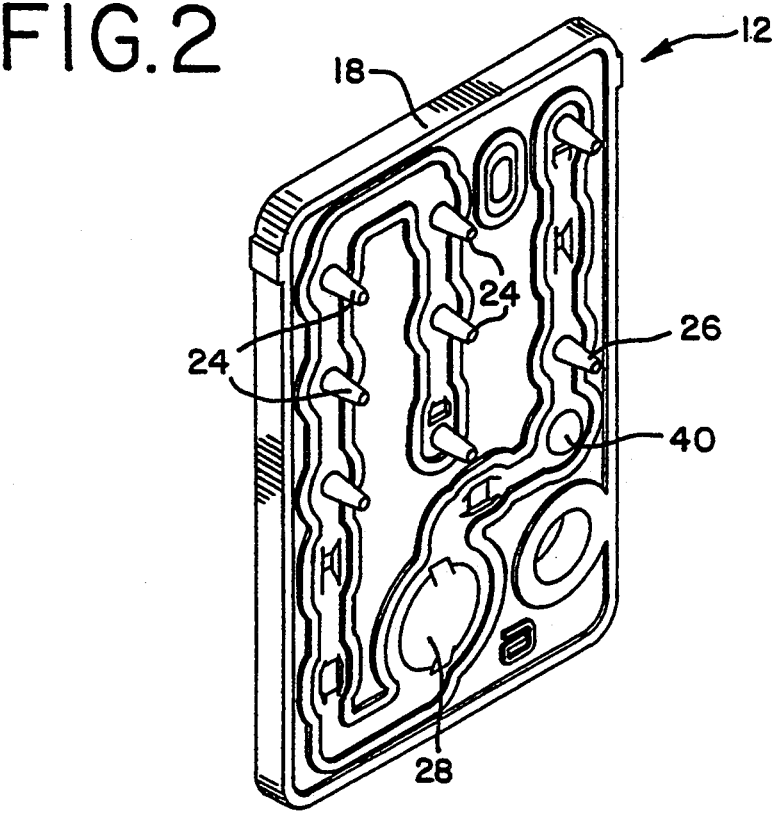
FIG. 2 is a perspective view of the pump cassette illustrated in FIG. 1.
Figure 3:
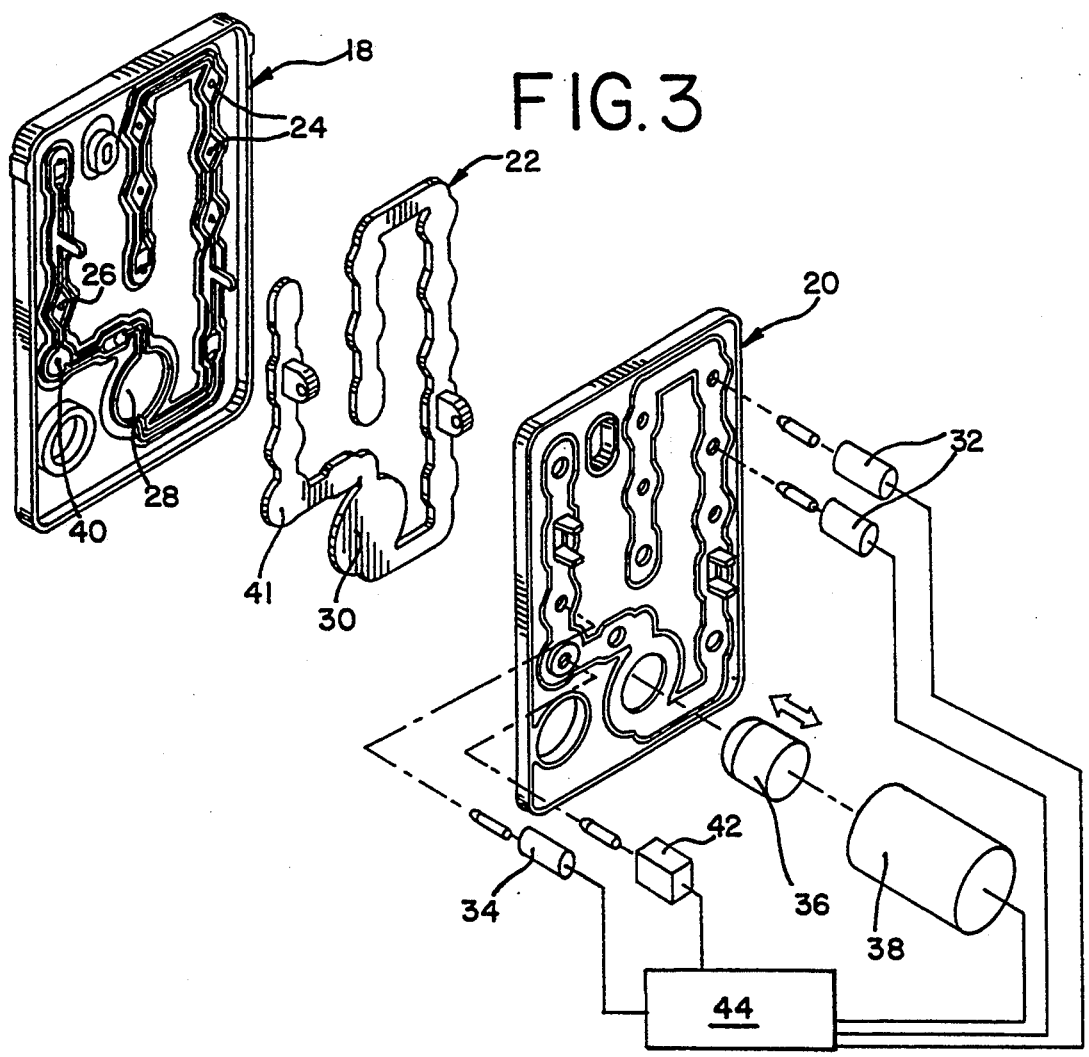
FIG. 3 is a diagrammatic, exploded perspective view illustrating the construction of the pump cassette shown in FIG. 2, and the manner in which components of the associated pump driver cooperate with the pump cassette.
Figure 4:
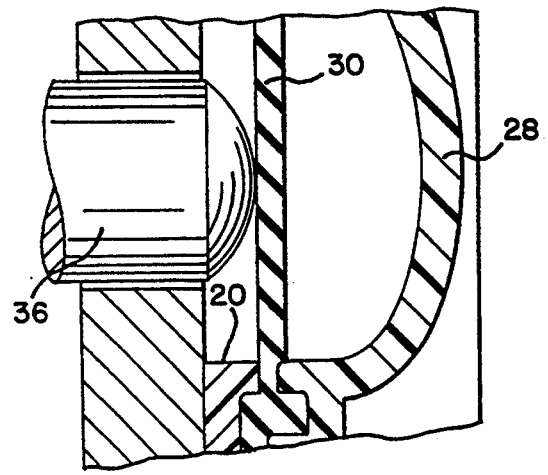
FIG. 4 is a fragmentary cross-sectional view illustrating a pump chamber of the pump cassette of the present system.

U.S. patent application Ser. No. 07/444,459, filed Dec. 1, 1989, now U.S. Pat. No. 5,064,774 issued Nov. 11, 1991, hereby incorporated by reference, discloses in greater detail features of the present solution pumping system. The disposable pump cassette 12 of the system, as particularly illustrated in FIGS. 2 and 3, includes a cassette body comprising juxtaposed front and rear body members 18 and 20, and a membrane-like elastomeric diaphragm 22 positioned in sandwich-like relationship between the front and rear cassette members.

The front and rear cassette members are joined to each other, such as by ultrasonic welding, such that the rear cassette member holds the elastomeric diaphragm 22 in tightly conforming relationship with the front cassette member 18. In this way, the diaphragm and the front cassette member together define a liquid flow path through which liquid flows within the cassette.

The cassette includes at least one, and preferably a plurality, of liquid inlets 24 which are configured to be joined via suitable tubing to containers of the various solutions to be compounded. The cassette further includes at least one liquid outlet 26 which is connected by suitable tubing to the container which receives the solution admixture being prepared.

Pumping of liquid through the cassette is effected by a self-contained positive displacement pump of the assembly. In particular, the front cassette member 18 includes a bowl-like pump chamber 28, with the diaphragm 22 including a pump portion 30 positioned adjacent to the pump chamber 28.

Control of liquid flow through the cassette is effected by a plurality of valve actuators of the pump driver 14, which in the illustrated embodiment are solenoid-operated. The valve actuators are operable through openings defined by the rear cassette member 20, with the actuators acting against respective portions of the diaphragm 22 to cooperate in a valve-like manner with valve seats defined by the front cassette member 18. Thus, each of the various liquid inlets 24 is controlled by a respective valve actuator 32, with the liquid outlet 26 similarly controlled by a respective valve actuator 34.

Operation of the positive displacement pump of the cassette is effected by a reciprocable pump piston or plunger 36 of the pump driver 14. Operation of the pump is in accordance with above-referenced U.S. Pat. No. 4,639,245, to Pastrone et al. Essentially, liquid flow is effected by reciprocation of the pump piston 36 in timed relation to operation of inlet and outlet actuators 32 and 34. A reversible stepping motor 38, acting through a suitable threaded connection, provides reciprocable stroking of the pump piston for alternately deforming and relaxing the pump portion 30 of the diaphragm 22, thus effecting positive displacement of liquid in the pump chamber 28. During the advancing stroke of the pump piston 36, the diaphragm portion 30 is displaced into the pump chamber, with outlet 26 being opened by appropriate operation of its actuator 34. Liquid displacement on the order of 0.75 ml is typical in a current embodiment. During the return stroke of the pump piston, the outlet is closed, and an appropriate one of the inlets 24 is opened by operation of its respective actuator 32. During the return stroke, the resilient pump portion 30 of the diaphragm creates a negative pressure within the pump chamber, thus refilling the chamber with liquid for completing the pump cycle.

In order to monitor liquid pressures created within the pump cassette by the positive displacement pump, the present system preferably includes a pressure sensor 42 incorporated into pump driver 14. Front cassette member 18 defines a pressure chamber 40, with the diaphragm 22 including a portion 41 adjacent the pressure chamber, which portion 41 is engaged by a probe-like portion of the pressure sensor 42. The pressure sensor 42 is operatively connected with automated, programmable controls 44 of the present system. The controls 44 are preferably integrated into the pump driver 14, with the controls operatively connected with the various valve actuators, stepper motor 38, and other sensors of the system for effecting integrated operation thereof.

Operation of the present system is effected in a manner which acts to minimize peak pumping pressures within the cassette 12, while maximizing liquid output of the device. In essence, this is achieved by operating the pump piston 36, and thus the positive displacement pump of the cassette, in a manner which creates a "square" pressure waveform. While the waveform is not truly "square" a practical impossibility, it is contemplated that during each pumping cycle, the system pressure is rapidly increased to the desired maximum, held at that desired limit until liquid from pump chamber 28 is displaced, and thereafter effecting refilling of the pump chamber as quickly as possible for the subsequent pump cycle. This is achieved by selectively varying the velocity of the pump piston during each advancing stroke, and preferably also during the return stroke.

As will be recognized by those familiar with the art, this mode of operation is in significant distinction from previous systems. In previous arrangements, operation of the pump piston has been at a constant velocity during the advancing stroke, and at the same or a different constant velocity during the return stroke. During development of the present system, by which maximum output can be obtained, it was recognized that operation of the pump piston at a constant velocity during the advancing stroke can undesirably result in either an excessive pressure "spike" or failure to reach the maximum permissible pressure of the system.

Figure 5:
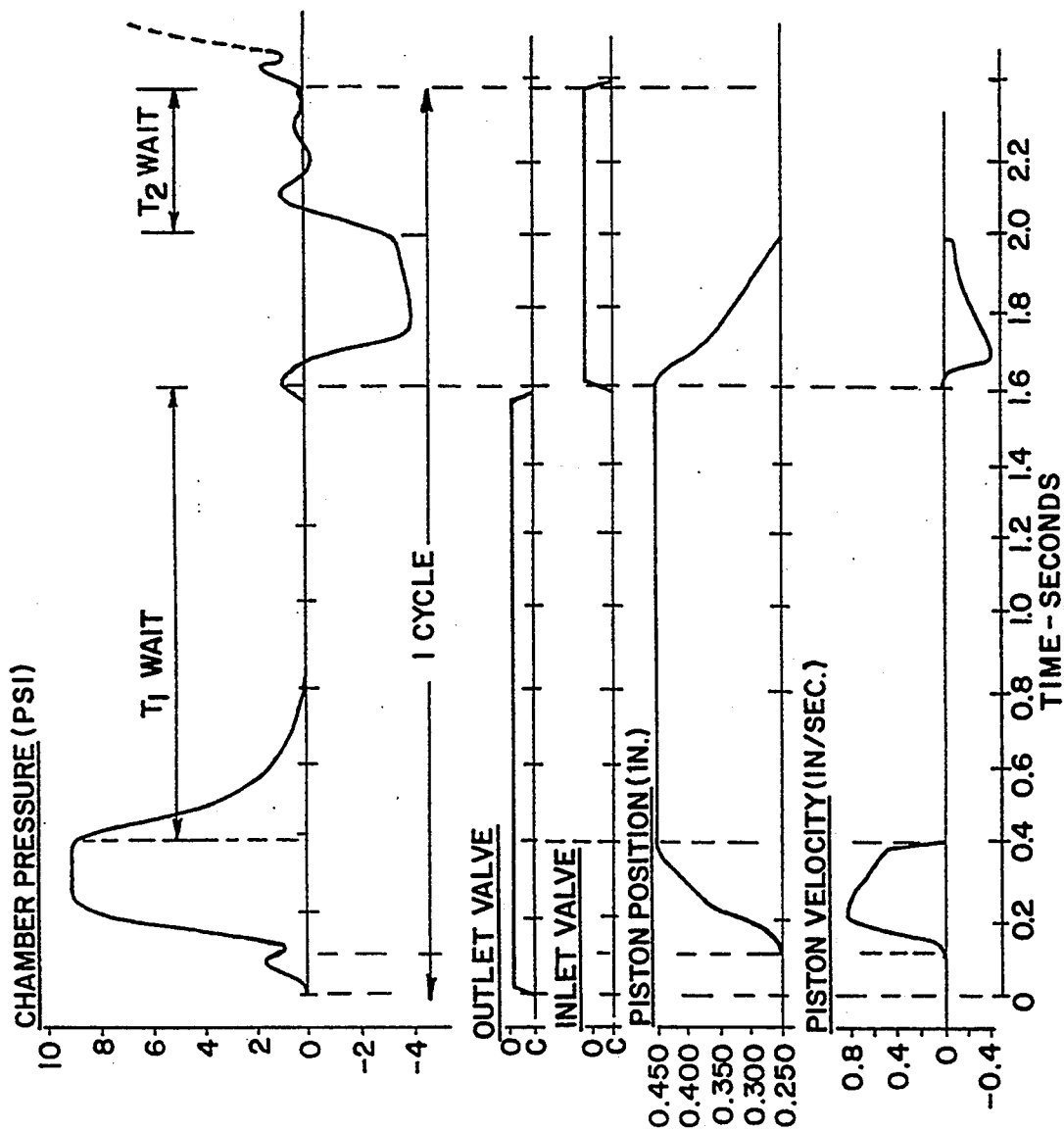
FIG. 5 illustrates a series of timing diagrams illustrating the operation of the present pumping system during a pump cycle.

FIG. 5 illustrates timing diagrams associated with a single pump cycle, i.e., one advancing stroke and return stroke of the pump piston 36 acting in cooperation with the pump portion 30 of the diaphragm 32. Most notably, it will be observed that "spikes" or "peaks" in the chamber pressure are avoided, but rather, pressure is held at or near its desired maximum for a sufficient period to effect the desired displacement of liquid from the pump chamber.

As will be further observed from the timing charts in FIG. 5, the velocity of pump piston 36 is controlled to prevent the creation of any pressure "spikes". While the piston is accelerated as quickly as possible, while avoiding excessive pressure, the velocity of the piston is thereafter adjusted and decreased to hold the pump pressure relatively constant at the maximum desired value. Thus, a relatively "square" pressure waveform is created during the advancing stroke of the pump piston as liquid is displaced from the pump chamber 28.

As further illustrated in the timing charts, the controls 44 operate to create a delay, $T_1$, in the closing of the liquid outlet of the cassette (and the opening of the liquid inlet) until the liquid pressure within the cassette returns substantially to zero subsequent to the advancing stroke of the pump piston. The length of the delay is dependent upon the flow resistance of the system, liquid viscosity, and the compliance of the system, with reduction of each of these system characteristics likewise permitting a reduction in the delay $T_1$.

After the pressure within the system substantially returns to zero, the outlet of the system is closed, and the liquid inlet opened. The stepper motor 38 is operated to effect a return stroke of the pump piston, with the resilience of the pump portion 30 of the diaphragm creating a negative pressure within the pump chamber for refilling it with liquid. Precise control of the present system is facilitated by operating the pump piston during its return stroke such that the pump piston remains in engagement with the pump diaphragm. The rate at which the piston is retracted is limited by the compliance of the diaphragm. Again, it is contemplated that the piston velocity be selectively varied to achieve rapid filling of the pump chamber while maintaining the pump piston in engagement with the diaphragm portion 30.

After the pump chamber refills with liquid, it is again desirable to delay valve actuation until pressure within the system returns substantially to zero. This is represented in the timing charts of FIG. 5 by delay $T_2$, during which the inlet of the cassette is kept open prior to reopening of the outlet of the cassette. As will be observed, the pressure in the system fluctuates slightly as the chamber refills, with this pressure undulation or "ringing" due to the inertia of solution within the system, and compliance of the diaphragm. By delaying closing of the inlet, and opening of the outlet, uniform, stroke-to-stroke, filling of the pump chamber is assured.

The stepper motor of the present system is preferably operated by the automatic controls to vary the pump piston velocity generally in accordance with the illustrated timing charts. In a present embodiment of the system, the velocity of the pump piston is controlled by selectively varying the dwell periods between successive driving steps of the stepper motor. Naturally, the precise manner in which piston velocity is controlled can be varied in accordance with the type of drive arrangement for the pump piston.

The provision of the pressure sensor 42, including the probe portion in engagement with the portion 41 of the diaphragm 22, desirably provides a feedback signal to the controls 44 for adjusting operation of the system. This is particularly desirable in view of the varying viscosities of different solutions pumped through the system, with higher viscosity solutions ordinarily creating higher pumping pressures. By monitoring pressure in the cassette, the controls 44 can be operated to automatically alter the "profile" of piston movement, thereby altering the pumping pressure profile of the system. Thus, excessive pressures can be avoided. While a current embodiment includes a plurality of discrete pumping profiles, which permit the system to change from one profile to another depending on pressure readings, it is within the purview of the present invention to provide a continuously variable system so that the pressure sensor provides a feedback signal to permit operation of the pump piston for maximum output at all times.

Additionally, controls of the present system can be programmed to vary the "piston profile" depending upon which solution is being pumped during compounding of a solution admixture. The viscosity characteristics of various solutions are well-known, and can be readily integrated into the program of the controls. Thus, selection of the desired piston profile for optimum pumping can be achieved without necessarily relying upon the feedback provided by pressure sensor 42.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover, by the appended claims, all such modifications as fall within the scope of the claims.

What is claimed is:

1. A solution pumping system, comprising:
    a pump driver including a reciprocable pump piston, and
    associated pump means in operative association with said pump piston of said pump driver,
    said system including a liquid inlet, a liquid outlet, and a liquid flow path for joining said inlet and outlet in fluid communication,
    said pump means being joined with said flow path for pumping liquid from said inlet to said outlet, via said flow path, by reciprocation of said pump piston, wherein said pump piston cooperates with said pump means to pump means with liquid during an advancing stroke of said pump piston and to fill said pump means with liquid during a return stroke of said pump piston,
    said system further including control means for controlling operation of said pump piston of said pump driver, said control means acting to minimize peak pressures created by said pump means while maximizing liquid output of said pump means, by selectively varying the velocity of the pump piston during the advancing stroke by accelerating the piston to a preselected maximum velocity and then decreasing the velocity for a selected time interval.

2. A solution pumping system in accordance with claim 1, wherein
    said system includes pressure sensor means operatively associated with said pump means for sensing liquid pressure created by said pump means, said pressure sensor means being operatively connected with said control means to reduce the liquid pressure created by said pump means when the pressure exceeds a predetermined value.

3. A solution pumping system in accordance with claim 1, wherein
    said pump means comprises a pump chamber, and a resilient pump diaphragm positioned adjacent to said chamber, said pump piston being engageable with said pump diaphragm so that during said advancing stroke of said pump piston, said diaphragm is displaced into said pump chamber for pumping liquid therefrom from said inlet to said outlet.
    said pump chamber refilling with liquid during said return stroke as said resilient diaphragm creates a negative pressure within said pump chamber, said control means operating said pump piston during said return stroke so that said pump piston remains in engagement with said pump diaphragm.

4. A solution pumping system in accordance with claim 1, wherein
    said pump driver includes a stepper motor operatively connected to said pump piston for advanced and retracting said pump piston by individual driving steps separated by dwell periods, said control means controlling the velocity of said pump piston by selectively varying the length of the dwell periods between successive driving steps of said stepper motor.

5. A solution pumping system, comprising:

a pump driver, said pump driver including a reciprocable pump piston, and a plurality of valve actuators; and a pump cassette positionable in operative association with said pump driver, said pump cassette including at least one liquid inlet, at least one liquid outlet, a liquid flow path for joining said inlet and said outlet in fluid communication, and pump means operatively driven by the pump piston of said associated pump driver for pumping liquid from a selected liquid inlet to a selected liquid outlet via said flow path, said pump means comprising a pump chamber, and a resilient pump diaphragm positioned adjacent the pump chamber for engagement with said pump piston, so that said diaphragm is displaced into said chamber during an advancing stroke of said pump piston, and said chamber is refilled with liquid during a return stroke of said pump piston as said resilient diaphragm creates a negative pressure within said chamber, said system including control means for controlling operation of said pump means by controlling the velocity of said pump piston during said advancing stroke by accelerating the piston to a preselected maximum velocity and then decreasing the velocity for a selected time interval to act to minimize peak pressures created by said pump means while maximizing liquid output of said pump means.

6. A solution pumping system in accordance with claim 5, wherein said pump driver includes pressure sensor means, including a probe engageable with said pump cassette, for sensing liquid pressure created by said pump means, said pressure sensor means being operatively connected with said control means to reduce the liquid pressure created by said pump means by varying the piston velocity when the pressure exceeds a predetermined value.

7. A solution pumping system in accordance with claim 6, wherein said control means operates to control opening and closing of said liquid inlet and said liquid outlet by controlling selected ones of said valve actuators respectively operatively associated therewith, said control means operating to delay closing of said liquid outlet and opening of said liquid inlet until the liquid pressure within said pump cassette returns substantially to zero subsequent to said advancing stroke of said pump piston, said control means operating to delay closing of said liquid inlet and opening of said liquid outlet until the liquid pressure within said pump cassette returns substantially to zero subsequent to the return stroke of said pump piston and refilling of said pump chamber.

8. A method of operating a solution pumping system including a pump driver having a reciprocal pump piston, and associated pump means in operative association with said pump piston, said method comprising the steps of:

reciprocally moving said pump piston for cooperation with said pump means, so that during an advancing stroke of said piston, liquid is pumped from said pump means, and during a return stroke of said piston said pump means refills with liquid, and selectively varying the velocity of said pump piston by accelerating the piston to a preselected maximum velocity and then decreasing the velocity for a selected time interval to act to minimize peak pressures created by said pump means during said advancing stroke while maximizing liquid output of said pump means.

9. A method of operating a pumping system in accordance with claim 8, including:

sensing the pressure created by said pump means, and reducing the velocity of said pump piston during the advancing stroke thereof when liquid pressure within said cassette exceeds a predetermined value.

10. A method of operating a pumping system in accordance with claim 8, including reciprocally moving said pump piston with a stepper motor operatively connected thereto, causing the pump piston not to move during at least one dwell period and controlling the velocity of said pump piston by selectively varying the dwell periods between successive driving steps of said stepper motor.

11. A method of operating a pumping system in accordance with claim 8, including delaying successive advancing and return strokes of said pump piston until liquid pressure created by said pump means returns substantially to zero.

* * * * *